US006890724B2

(12) United States Patent
Anderson et al.

(10) Patent No.: US 6,890,724 B2
(45) Date of Patent: May 10, 2005

(54) METHODS AND COMPOSITIONS FOR NEURAL PROGENITOR CELLS

(75) Inventors: David J. Anderson, Altadena, CA (US); Li-Ching Lo, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 08/719,571

(22) Filed: Sep. 25, 1996

(65) Prior Publication Data

US 2002/0132987 A1 Sep. 19, 2002

Related U.S. Application Data

(60) Provisional application No. 60/025,579, filed on Sep. 6, 1996, now abandoned.

(51) Int. Cl.[7] .......................... C07K 16/28; C12N 5/06; G01N 33/533; G01N 33/543; G01N 33/567

(52) U.S. Cl. ..................... 435/7.21; 435/7.95; 435/325; 435/334; 435/344.1; 435/352; 436/503; 436/518; 436/172; 530/387.7; 530/388.22; 530/388.85; 530/389.7; 530/391.5

(58) Field of Search .......................... 530/387.1, 387.7, 530/388.22, 388.8, 388.85, 389.7, 391.3, 839, 843; 435/7.21, 7.23, 7.8, 7.95, 70.21, 960, 325, 352, 334, 344.1; 436/503, 518, 536, 548, 172; 935/102, 104

(56) References Cited

U.S. PATENT DOCUMENTS 5,411,883 A * 5/1995 Boss et al. ................ 435/240.2

OTHER PUBLICATIONS

Martucciello et al., Mar. 1995. Immunohistochemical localization of RET protein in Hirschsprung's disease. J. Ped. Surg. 30(3): 433–436.*
Harlow et al., 1988. *Antibodies. A Laboratory Manual*, Cold Spring Harbor Laboratory, Cold Spring Harbor. pp. 72–77.*
Campbell, 1984. *Monoclonal Antibody Technology*, Elsevier, Amsterdam. pp. 1–4 and 29.*
Maurer et al., 1980. Proteins and polypeptides as antigens. Meth. Enzymology 70: 49–70.*
Tsuzuki et al., Jan. 1995. Spatial and temporal expression of the *ret* proto–oncogene product in embryonic, infant and adult rat tissues.*
Nakamura et al., 1994. Expression of the *ret* proto–oncogene product in human normal and neoplastic tissues of neural crest origin. J. Pathol. 172: 255–260.*
Reynolds et al., 1992. EGF–responsive progenitor cells in the embryonic human central nervous system. Soc. Neurosci. Abstr. 18 (1–2): 1107, Abstract #467.3.*
Vescovi et al., 1993. Continual proliferation of EGF–dependent progenitor cells of the embryonic human CNS in vitro. Soc. Neurosci. Abstr. 19 (1–3): 871, Abstract #360.12.*

Sieber–Blum, M., "Mechanisms of Neural Crest Diversification," *Comments Developmental Neurobiology*, 1(4):225–249 (1990).
Anderson, D.J., "Cell and Molecular Biology of Neural Crest Cell Lineage Diversification," *Current Opionion in Neurobiology*, 3:8–13 (1993).
Lo et al., "MASH–1: A Marker and a Mutation for Mammalian Neural Crest Development," *Perspectives on Developmental Neurobiology*, 2(2):191–201 (1994).
Deville et al., "Developmental Potentialities of Cells Derived from the Truncal Neural Crest in Clonal Cultures," *Developmental Brain Research*, 66:1–10 (1992).
Bronner–Fraser and Fraser, "Cell Lineage Analysis Shows Multipotentiality of Some Avian Neural Crest Cells," *Nature*, 335:161–164 (1988).
Frank and Sanes, "Lineage of Neurons and Glia in Chick Dorsal Root Ganglia: Analysis in vivo with a Recombinant Retrovirus," *Development III*, pp. 895–908 (1991).
Sieber–Blum and Cohen, "Clonal Analysis of Quail Neural Crest Cells: They are Pluripotent and Differentiate in Vitro in the Absence of Noncrest Cells," *Devel. Biol.*, 80:96–106 (1980).
Baroffio et al., "Clone Forming Ability and Differentiation Potential of Migratory Neural Crest Cells," *PNAS USA*, 85:5325–5329 (1988).
Ito et al., "In vitro Clonal Analysis of Mouse Neural Cress Development," *Dev. Biol.*, 157:517–525 (1993).
Stemple and Anderson, "Linear Diversification of the Neural Crest In Vitro Investigations," *Dev. Biol.*, 159:12–23 (1993).
Le Lievre et al., "Restrictions of Developmetnal Capabilities in Neural Crest Cell Derivatives as Tested by in Vivo Transplantation Experiments," *Dev. Biol.*, 77:362–378 (1980).
Le Douarin, "Cell Line Segregation During Peripheral Nervous System Ontogeny," *Science*, 231:1515–1522 (1986).
Artinger and Bronner–Fraser, "Partial Restriction in The Developmental Potential of Late Emigrating Avian Neural Crest Cells," *Dev. Biol.*, 149:149–157 (1992).
Duff et al., "In vitro Clonal Analysis of Progenitor Cell Patterns in Dorsal Root and Sympathetic Ganglia of the Quail Embryo," *Dev. Biol.*, 147:451–459 (1991).
Hall and Landis, "Early Commitment of Precursor Cells from the Rat Superior Cervical Ganglion to Neuronal of Nonneuronal Fates," *Neuron*, 6:741–752 (1991).
Deville et al., "Developmental Potentials of Enteric Neural Crest–Derived Cells in Clonal and Mass Cultures," *Dev. Biol.*, 163:141–151 (1994).
Pachnis et al., "Expression of the c–ret proto–oncogene During Mouse Embryogenesis," *Development* 119:1005–1017 (1993).

(Continued)

*Primary Examiner*—Christopher L. Chin
*Assistant Examiner*—James L. Grun
(74) *Attorney, Agent, or Firm*—Mintz Levin Cohn Ferris Glovsky and Popeo PC; Ivor R. Elrifi

(57) ABSTRACT

The invention relates to methods and compositions for the isolation of neural progenitor cells.

9 Claims, 1 Drawing Sheet

OTHER PUBLICATIONS

Schuchardt et al., "Defects in the Kidney and Enteric Nervous System of Mice Lacking the Tyrosine Kinase Receptor Ret," *Nature*, 367:380–383 (1994).

Edery et al., Mutations of the RET Proto–Oncogene in Hirschsprung's Disease, *Nature*, 367:378–380 (1994).

Guillemot et al., "Dynamic Expression of the Murine Achaete–Sculo Homologue Mash–1 i the Developing Nervous System," *Mech. Devel.*, 42:171–185 (1993).

Lo et al., "Mammalian achaete–scute Homolog 1 is Transiently Expressed by Spatially Restricted Subsets of Early Neuroepithelial and Neural Crest Cells," *Genes & Dev.*, 5:1524–1537 (1991).

Hesketh, ed., "The Oncogene Facts Book," Academic Press Ltd.: San Diego, pp. 241–245 (1995).

Lo and Anderson, "Postmigratory Neural Crest Cells Expressing c–RET Display Restricted Developmental and Proliferative Capacities," *Neuron*, 15:527–539 (1995).

McKay, "The Origins of Cellular Diversity in the Mammalian Central Nervous System," *Cell*, 58:815–821 (1989).

Sanes, "Analysing Cell Lineage with a Recombinant Retrovirus," *Trends Neurosci.*, 12:21–28 (1989).

McConnell, "The Generation of Neuronal Diversity in the Central Nervous System," *Ann. Rev. Neurosci.*, 14:269–300 (1991).

Stemple and Anderson, "Isolation of a Stem Cell for Neurons and Glia from the Mammalian Neural Crest," *Cell*, 71:973–985 (1992).

Wren et al., In Vitro Analysis of the Origin and Maintenance of O–2A$^{adult}$Progenitor Cells, *Journal of Cell Biology*, 116:167–176 (1992).

Davis and Temple, "A Self–Renewing Multipotential Stem Cell in Embryonic Rat Cerebral Cortex," *Nature*, 372:263–266 (1994).

Spangrude et al., "Purification and Characterization of Mouse Hematopoietic Stem Cells," *Science*, 241:58–62 (1988).

Altman., "Autoradiographic and Histological Studies of Postnatal Neurogenesis. IV. Cell Proliferation and Migration in teh Anterior Forebrain, with Special Reference to Persisting Neurogenesis in teh Olfactory Bulb," *J. Comp. Neurol.*, 137:433–458 (1969).

Kaplan and Hinds, "Neurogenesis in the Adult Rat: Electron Microscopic Analysis of Light Radioautographs," *Science*, 197:1092–1094 (1977).

Wolswijk and Noble, "Identification of an Adult–Specific Glial Progenitor Cell," *Development*, 105:387–400 (1992).

Reynolds and Weiss, "Generation of Neurons and Astrocytes from Isolated Cells of the Adult Mammalian Central Nervous System," *Science*, 255:1707–1710 (1992).

Lois and Alvarez–Buylla, "Proliferating Subventricular Zone Cells in the Adult Mammalian Forebrain Can Differentiate into Neurons and Glia," *PNAS USA.*, 90:2074–2077 (1993).

Morshead et al., "Neural Stem Cells in the Adult Mammalian Forebrain: A Relatively Quiescent Subpopulation of Subependymal Cells," *Neuron*, 13:1071–1082 (1994).

Ogawa, "Differentiation and Proliferation of Hematopoietic Stem Cells," *Blood*, 81:2844–2853 (1993).

Anderson, "The Neural Crest Cell Lineage Problem: Neuropolesis?" *Neuron*, 3:1–12 (1989).

LeDouarin et al., "Glial Cell Lineages in the Neural Crest," *Glia*, 4:175–184 (1991).

\* cited by examiner

US 6,890,724 B2

METHODS AND COMPOSITIONS FOR NEURAL PROGENITOR CELLS

This is a continuation-in-part application of U.S. Application No. 60/025,579, filed Sep. 6, 1996, abandoned.

FIELD OF THE INVENTION

The invention relates to methods and compositions for the isolation of neural progenitor cells.

BACKGROUND OF THE INVENTION

The nervous system, like the immune system, develops from multipotent progenitor cells. The existence of neural progenitor cells that generate multiple types of neurons and glia has been well documented both in vivo and in vitro in the CNS and PNS (for reviews, see McKay, R. D. G., *Cell* 58:815–821 (1989); Sanes, J. R., *Trends Neurosci.* 12:21–28 (1989); McConnell, S. K., *Ann. Rev. Neurosci.* 14:269–300 (1991)). In some cases, moreover, such multipotent cells have been shown to be capable of self-renewal at the single-cell level (Stemple, D. L. and Anderson, D. J., *Cell* 71:973–985 (1992); Wren, D., Wolswijk, G. and Noble, M., *Journal of Cell Biology.* 116:167–176 (1992); Davis, A. and Temple, S., *Nature* 372:263–266 (1994) suggesting that they may be analogous to self-renewing hematopoietic stem cells (Spangrude, G. J., Heimfeld, S. and Weissman, I. L., *Science* 241:58–62 (1988)). In support of this idea, there is evidence in the CNS for the persistence of some kinds of neuronal and glial progenitors into adulthood (Altman, J., *J. Comp. Neurol.* 137:433–458. (1969); Kaplan, M. S. and Hinds, J. W., *Science* 197:1092–1094 (1977); Wolswijk, G. and Noble, M., *Development* 105:387–400 (1992); Reynolds, B. A. and Weiss, S., *Science* 255:1707–1710 (1992); Lois, C. and Alvarez-Buylla, A., *Proc. Natl. Acad. Sci. USA* 90:2074–2077 (1993); Morshead, C. M., Reynolds, B. A., Craig, C. G., McBurney, M. W., Staines, W. A., Morassutti, D., Weiss, S. and van der Kooy, D., *Neuron* 13:1071–1082 (1994)).

The existence of multipotent neural progenitors raises the question of how these cells generate their differentiated derivatives. On the one hand, cell fate could be assigned by lineage or by other cell-autonomous mechanisms. On the other hand, cell fate could be influenced or determined by cell-extrinsic signals. A popular idea to explain hematopoiesis is that both types of mechanisms operate, so that multipotent stem cells generate progenitors committed to one or more sublineages, which then proliferate, survive and differentiate in response to specific growth factors (Ogawa, M., *Blood* 81:2844–2853 (1993)). Similar "neuropoietic" models have also been invoked to explain cell lineage diversification in the nervous system (Anderson, D. J., *Neuron* 3:1–12 (1989); Sieber-Blum, M., *In: Comments Developmental Neurobiology* 1:225–249 (1990); LeDouarin, N., Dulac, C., Dupin, E. and Cameron-Curry, P., *Glia.* 4:175–184 (1991), although evidence in support of such models has been relatively scant and indirect (for review, see Anderson, D. J., *Curr. Opin. Neurobiology* 3:8–13 1993).

The neural crest represents a good model system in which to investigate the process of neural cell lineage diversification in vertebrates because it is relatively simple and experimentally accessible (LeDouarin, N. M., *Cambridge University Press. Cambridge, UK* (1982)). In vivo lineage-tracing studies (Bronner-Fraser, M. and Fraser, S., *Nature* 335:161–164 (1988); Frank, E. and Sanes, J. R., *Development* 111 pp 895–908 (1991) and in vitro clonal analyses (Sieber-Blum, M. and Cohen, A., *Devel. Biol.* 80:96–106 (1980); Baroffio, A., Dupin, E and Le Douarin, N. M., *Proc. Natl. Acad. Sci. USA* 85:5325–5329 (1988); Stemple, D. L. and Anderson, D. J., *Cell* 71:973–985 (1992); Ito et al., 1993) have demonstrated that many neural crest cells are multipotent at the time they emigrate from the neural tube in both avian and mammalian embryos. In the rate, moreover, serial cell cloning experiments have shown that such multipotent cells are capable of at least limited self-renewal in vitro (Stemple, D. L. and Anderson, D. J., *Cell* 71:973–985 (1992). Furthermore, the fate of such multipotent cells can be influenced by environmental signals (for review, see Stemple, D. L. and Anderson, D. J., *Devel. Biol.* 159:12–23 (1993)).

These experiments did not address the issue of whether neural crest cells undergo progressive restrictions in developmental potential. That such restrictions may occur has been suggested from studies of transplanted or cultured avian neural crest cell populations (Le Lievre, C. S., Schweizer, G. G., Ziller, C. M. and Le Douarin, N. M., *Developmental Biology* 77:362–378 (1980); Le Douarin, N. M., *Science* 231:1515–1522 (1986); Artinger, K. B. and Bronner-Fraser, M., *Dev. Biol.* 149:149–157 (1992) or from clonal analysis of postmigratory crest cells in peripheral ganglia (Duff, R. S., Langtimm, C. J., Richardson, M. K. and Sieber-Blum, M., *Dev. Biol.* 147:451–459 (1991); Hall, A. K. and Landis, S. C., *Neuron* 6:741–752 (1991); Deville, F. S.-S. C., Ziller, C. and Le Douarin, N., *Dev. Brain Res.* 66:1–10 (1992); Deville, F. S.-S. C., Ziller, C. and Le Douarin, N. M., *Dev. Biol.* 163:141–151 (1994). However, in the transplantation studies that manipulated the cells' environment, there was no analysis of single cells, and in the single cell culture experiments, there was no manipulation of the cells' environment. To date, there has been no study in which postmigratory neural crest cells in clonal culture have been challenged by exposure to environmental signals known to influence the fate of early migratory cells.

c-RET is an orphan receptor tyrosine kinase is one of the earliest surface markers that distinguishes postmigratory from early migrating neural crest cells (Pachnis, V., Mankoo, B. and Costantini, F., *Development* 119, in press.; Lo, L., Guillemot, F., Joyner, A. L. and Anderson, D. J., *Persp. Dev. Neuro.* 2:191–201 (1994)). RET is not simply a marker for enteric progenitors but is also essential for their proper development, as shown by genetic studies in both mice (Schuchardt, A., D'Agati, V., Larsson-Blomberg, L., Costantini, F. and Pachnis, V., *Nature* 367:380–383 (1994)) and humans (Edery, P., Lyonnet, S., Mulligan, L. M., Pelet, A., Dow, E., Abel, L., Holder, S., Nihoul-Fekete, C., Ponder, B. A. J. and Munnich, A., *Nature* 367:378–380 (1994). In situ hybridization experiments have indicated that RET is not expressed by early migrating trunk neural crest cells in vivo but is expressed after these cells have aggregated to form the primordia of autonomic ganglia (Pachnis, V., Mankoo, B. and Costantini, F., *Development* 119, in press.).

Both Ret and Mash1 are regulatory genes essential for the development of subsets of autonomic neurons, as shown by targeted gene disruption experiments in mice (Guillemot, F. and Joyner, A. L., *Mech. Devel.* 42:171–185 1993); Schuchardt, A., D'Agati, V., Larsson-Blomberg, L., Costantini, F. and Pachnis, V., *Nature* 367:380–383 (1994)). In addition, both genes are initially expressed in otherwise morphologically and antigenically undifferentiated neural crest cells (Lo, L., Johnson, J. E., Wuenschell, C. W., Saito, T. and Anderson, D. J., *Genes & Dev.* 5:1524–1537 (1991).; Guillemot, F. and Joyner, A. L., *Mech. Devel.* 42:171–185 (1993); Pachnis, V., Mankoo, B. and Costantini, F., *Development* 119, in press.). While Ret is genetically essential for the development of all enteric neurons, the precise developmental operation it controls is not yet established.

The fact that Ret and Mash1 are expressed sequentially (Guillemot, F. and Joyner, A. L., Mech. Devel. 42:171–185 (1993); Lo, L., Guillemot, F., Joyner, A. L. and Anderson, D. J., Persp. Dev. Neuro. 2:191–201 (1994)) in the same cells and that both are required for the differentiation of at least a subpopulation of peripheral autonomic neurons raises the possibility that there is an interaction between these two genes. For example, signally through RET could lead to the expression of MASH1; conversely, MASH1 could be required for the maintenance or up-regulation of RET expression. However, though Ret is required for the differentiation of all enteric neurons (Schuchardt, A., D'Agati, V., Larsson-Blomberg, L., Costantini, F. and Pachnis, V., Nature 367:380–383 (1994)), it is not essential for the initial differentiation of sympathetic neurons. Conversely, Mash1 is required for sympathetic neuron differentiation (Guillemot, F. and Joyner, A. L., Mech. Devel. 42:171–185 (1993)) but not for the differentiation of some enteric neurons. These data suggest that Mash1 expression does not require Ret function in sympathetic neurons, and that Ret function does not require Mash1 expression in late-generated enteric neurons. Nevertheless, recent evidence indicates that early-generated enteric neurons, including the serotonergic subset, require Mash1 function (Blaugrund et al., submitted) as well as Ret function (Schuchardt, A., D'Agati, V., Larsson-Blomberg, L., Costantini, F. and Pachnis, V., Nature 367:380–383 (1994)). This leaves open the possibility that there is a genetic interaction between Ret and Mash1 within this enteric sublineage. The ability to isolate RET+ neural crest cells from embryos of various genotypes would permit a more detailed analysis of the functions and interactions of these and other regulatory genes involved in neural crest development, as well as of the mechanistic basis of developmental restriction within this population.

Accordingly, it is an object of the invention to provide methods and compositions for the enrichment and characterization of neural progenitor cells.

SUMMARY OF THE INVENTION

In accordance with the above objects, methods and compositions are provided for the enrichment and characterization of neural progenitor cells. Novel antigen and antibody compositions are provided for use in the subject methods, and for the further investigation of neural cell biology.

DETAILED DESCRIPTION OF THE INVENTION

Figure 1:
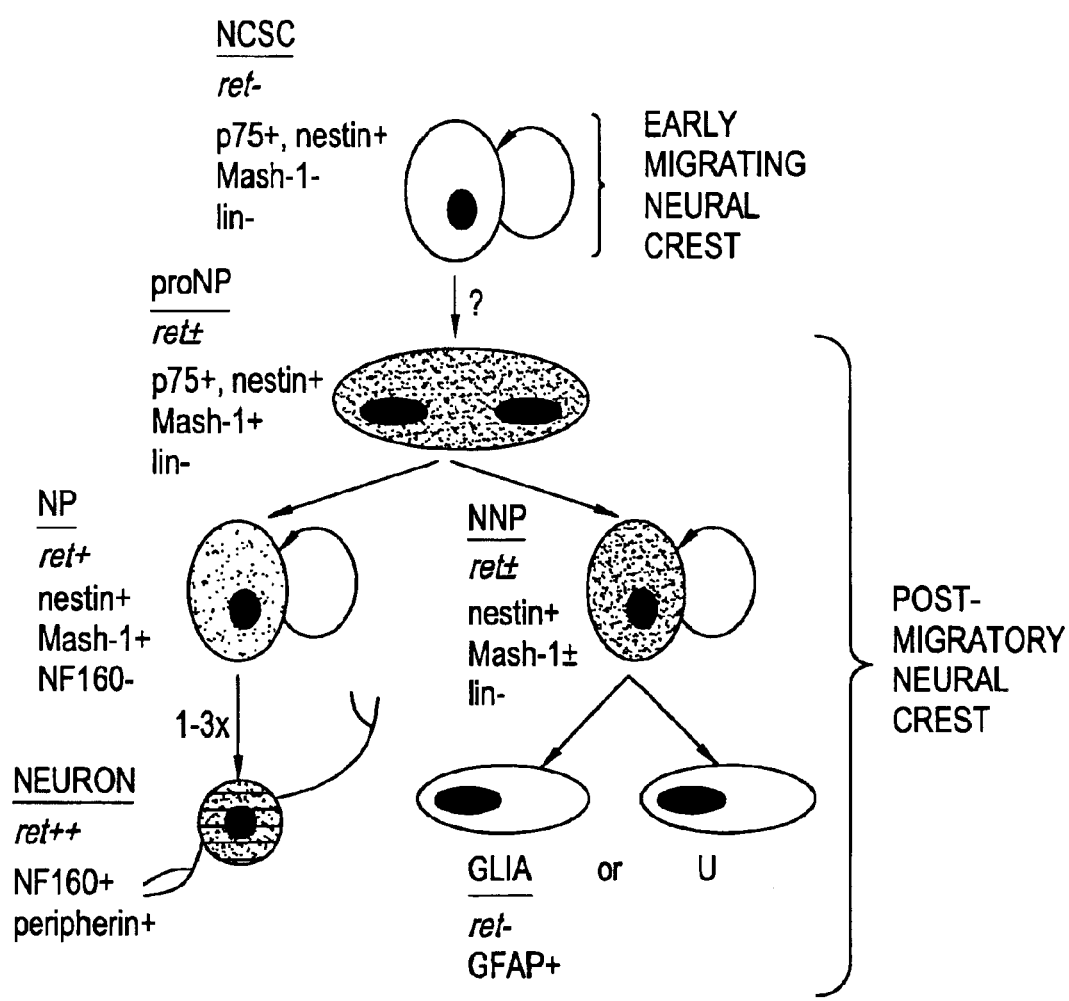
FIG. 1 depicts a model representing the putative lineage relationships between the progenitor cell types. The antigenic phenotype of each progenitor cell type is indicated. The proposed lineage relationships between these cells have not been demonstrated directly; in particular, it has not yet been shown that NCSCs can generate RET+ proNPs or NPs in vitro. The two differently shaded ovals in the proNP indicate the daughter nuclei of an asymmetrically dividing cell and are speculative. The progressively darker stippling in the cell bodies of proNPs, NPs and neurons indicates that the expression of RET is progressively higher in these three cell types. U, unidentified nonneuronal cells.

Methods and compositions are provided for the enrichment and characterization of neural progenitor cells of several types. The immediate progeny of the neural crest stem cell is believed to be neural progenitor cells, which are capable of giving rise to various cell types within one or more lineages, as is more fully described below. The progenitor cells are identified or selected through the use of novel reagents that specifically bind to the RET antigen, e.g. RET monoclonal antibody. The high tissue specificity of RET expression is particularly advantageous during enrichment for highly purified progenitor cell populations.

Molecules of interest in the subject methods are RET antigens, antibodies that specifically bind RET, and nucleic acid sequences encoding the RET antigen as described herein.

The sequence of RET is known from several organisms; see for example pages 241–245 of The Oncogene Facts Book, Hesketh ed., Academic Press Limited, 1995 and references cited therein, all of which are incorporated by reference. All or part of the sequence of RET may be used as a RET antigen. In the present invention, preferred RET antigens are all or part of the extracellular domain of RET. When part of the RET sequence is used as the RET antigen, antibodies generated to the antigen preferably specifically bind to the full length (native) sequence as well.

The RET antigen may be from mice, rats and other rodents, primates, and humans, with human RET antigens being preferred.

The RET antigen may be used to generate antibodies either alone or in combination with other components. Thus, purified RET antigens may be injected into animals for the generation of antibodies. Alternatively and preferably, as is outlined in the examples, the RET antigens may be made as a fusion construct with a fusion partner such as a lipid link or an anchoring signal, and the fusion construct expressed in cells such as chinese hamster ovary (CHO) cells, and the cells injected into the animals. Thus, in a preferred embodiment, the RET antigen is made as a phosphatidyl inositol (PI)-linked form such as is generally described in Devaux, B., Bjorkman, P. J., Stevenson, C., Griof, W., Elliott, J. F., Sagerstrom, C., Clayberger, C., Krensky, A. M. and Davis, M. M., Eur. J. Immunol. 21:2111–2119 (1991), hereby expressly incorporated by reference.

Antibodies to all or part of RET are of particular interest. Antibodies to the RET antigen are obtained by immunizing a xenogeneic immunocompetent mammalian host, including murine, rodentia, lagomorpha, ovine, porcine, bovine, etc. with RET antigens. The choice of a particular host is primarily one of convenience. Mice, rats, guinea pigs and hamsters are all preferred.

Immunizations are preformed in accordance with conventional techniques, where the RET antigen may be injected subcutaneously, intramuscularly, intraperitoneally, intravascularly, etc. Normally, from about $10^5$ to about $10^8$ cells will be used, which may be divided up into 1 or more injections, usually not more than about 8 injections, over a period of from about one to three weeks. The injections may be with or without adjuvant, e.g. complete or incomplete Freund's adjuvant, Specol, alum, etc. If desired, booster injections may be employed at 2 to 4 week intervals, usually there not being more than about 1 to 3 booster injections.

After completion of the immunization schedule, the antiserum may be harvested in accordance with conventional ways to provide polyclonal antisera specific for the RET antigens. The RET antibodies of the invention specifically bind to all or part of RET proteins. By "specifically bind" herein is meant that the antibodies bind to the protein with a binding constant in the range of at least $10^4$–$10^6$ $M^{-1}$, with a preferred range being $10^7$–$10^9$ $M^{-1}$.

Of particular interest are monoclonal antibodies. After completion of the immunization schedule the lymphocytes are harvested from the appropriate lymphoid tissue, e.g. spleen or draining lymph node, harvested, and fused with an appropriate fusion partner, usually a myeloma line, producing a hybridoma secreting a specific monoclonal antibody. Screening clones of hybridomas for the antigenic specificity of interest is performed in accordance with conventional methods.

Of particular interest are the monoclonal antibodies described in the Experimental section, 3A61d7, 3A61C6, and 2C42H1. Thus, in one embodiment, RET antibodies may be defined as antibodies which bind to the antigen recognized by the antibodies described in the Examples.

The subject antibodies may be produced as a single chain, instead of the normal multimeric structure. Single chain antibodies are described in Jost et al., J. Biol. Chem. 269:26267–26273 (1994), and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Methods of humanizing antibodies are known in the art. The humanized antibody may be the product of an animal having transgenic human immunoglobulin constant region genes (see for example International Patent Applications WO/90/10077 and WO 90/04036). Alternatively, the antibody of interest may be engineered by recombinant DNA techniques to substitute the CH1, CH2, CH3, hinge domains, and/or the framework residues with the corresponding human sequence (see WO 92/02190).

The use of Ig cDNA for construction of chimeric immunoglobul in genes is known in the art (Lui et al., Proc. Natl. Acad. Sci. 84:3439 (1987) and Lui et al., J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant region genes may be found in Kabat et al., *Sequences of Proteins of Immunological Interest*, N.I.H. publication no. 91-3242. Human C region genes are readily available from known clones. The chimeric, humanized antibody is then expressed by conventional methods.

Antibody fragments, such as Fv, F(ab')$_2$ and Fab may be prepared by cleavage of the intact protein, eg. by protease or chemical cleavage. Alternatively, a truncated gene is designed. For example, a chimeric gene encoding a portion of the F(ab')2 fragment would include DNA sequences encoding the CH1 domain and hinge region of the H chain, followed by a translational stop codon to yield the truncated molecule.

The subject antibodies have a number of in vivo and in vitro uses. Immunoselection with RET antibodies provides a means of purifying neuronal progenitor cells. The antibodies find use in diagnostics to detect or enumerate neuronal progenitor cells, dividing neuronal progenitor cells into functionally distinct sub-populations, isolation of progenitor cells, preparation of progenitors to produce mature neuronal cells, etc. Biological samples, e.g. neural crest derived cells, are assayed by any convenient immunoassay method for the presence of cells expressing RET bound by the subject antibodies. Assays may be performed on cell lysates, intact cells, frozen sections, etc.

The subject antibodies are particularity useful for the preparation of substantially pure neural progenitor cells. By "substantially pure" herein is meant that at least about 50% of the cells present after sorting are either neural progenitor cells or neurons, with at least about 70% preferred and at least about 90% particularly preferred. By "neural progenitor cells" herein is meant any one or a mixture of cells types, including proneuronal progenitors (proNP), nonneuronal progenitors (NNP), and neuronal progenitors (NP). All of these cell types contain the RET antigen as demonstrated by the binding of RET antibody and are thus RET+.

ProNP cells are characterized as being able to give rise to both neurons and glia (as well as other unidentified nonneuronal cells) and are thus considered multipotent. By "multipotent" herein is meant that a single cell is able to give rise to asymmetric daughter cells, as is known in the art, i.e. they are capable, under the conditions described, of self-regeneration and differentiation to some but not all types of neurons and glia in vitro. ProNP cells are also characterized as expressing: (1) nestin, a neuroepithilial stem cell marker (Lendahl, U., Zimmerman, L. B. and McKay, R. D. G., *Cell* 60:585:595 (1990)) also expressed by neural crest stem cells (NCSCs); Stemple, D. L. and Anderson, D. J., *Cell* 71:973–985 (1992); (2) the low affinity growth nerve growth factor (LNGFR) receptor, p75, also a surface marker of NCSCs (Stemple and Anderson, supra); (3) MASH1, a basic-helix-loop-helix transcriptional regulator (Lo, L., Johnson, J. E., Wuenschell, C. W., Saito, T. and Anderson, D. J., *Genes & Dev.* 5:1524–1537 (1991)), which is not expressed by NCSCs and thus serves as a distinguishing factor between proNP cells and NCSCs. ProNP cells do not express lineage markers such as neurofilaments, S100, glial fibrillary acidic protein (GFAP), sulfatide, myelin protein Po and peripherin. Neurofilaments are neuron-specific intermediate filament proteins. Three neurofilament (NF) proteins have been reported: NF68, a 68 kD protein also called NF-L (Light); NF160, a 160 kD protein also called NF-M (Medium); NF200, 200 kD protein also called NF-H (Heavy). Thus, proNP cells are characterized as being nestin+, p75+, RET+, MASH1+, and lin−.

Nonneuronal progenitor cells (NNP) are characterized as being RET+, nestin+, and MASH1+. In contrast to the proNP cells however, NNP cells are not capable of differentiation into neurons and glia, since only glia and possibly some as yet unidentified nonneuronal cells.

Neuronal progenitor (NP) cells are characterized by being RET+, nestin+, and MASH1+, but may or may not contain neuron lineage markers such as neurofilament. NP cells are further characterized by their commitment to forming neurons, as evidenced in two ways. First of all, NP cells demonstrate an insensitivity to glial growth factor (GGFII, also called neuregulin; Marchionni, M. A., Goodearl, A. D. J., Chen, M. S., Bermingham-McDonogh, O., Kirk, C., Hendricks, M., Danehy, F., Misumi, D., Sudhalter, J., Kobayashi, K., Wroblewski, D., Lynch, C., Baldassare, M., Hiles, I., Davis, J. B., Hsuan, J. J., Totty, N. F., Otsu, M., McBurney, R. N., Waterfield, M. D., Stroobant, P. and Gwynne, D., *Nature* 362:312–318 (1993)), a protein known to exert an instructive influence on trunk-derived NSCSs, repressing neuronal differentiation and promoting glial differentiation by most or all of the cells (Shah, N. M., Marchionni, M. A., Isaacs, I., Stroobant, P. W. and Anderson, D. J., *Cell* 77:349–360 (1994)). In addition, is has previously been demonstrated that neuronal differentiation from NCSCs is strongly inhibited or delayed on a substrate that contains fibronectin but not polylysine (Stemple, D. L. and Anderson, D. J., *Cell* 71:973:985 (1992)). NP cells, in contrast, when plated on fibronectin plates in the absence of polylysine, generally generated neurons, thus indicating that this substrate is unable to inhibit or delay neuronal differentiation. Thus, NP cells differentiate to neurons despite the presence of both soluble factors and extracellular matrix molecules that can inhibit neuronal differentiation by early migrating trunk NCSCs.

A subset of neural progenitor cells is separated from other cells on the basis of RET antibody binding, and may be further separated by binding to other surface markers known in the art, as is more fully outlined herein.

Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide, LDS). Red blood cells may be removed by elutriation, hemolysis, Ficoll-Paque gradients, etc. Any technique may be employed which is not unduly detrimental to the viability of the selected cells.

Conveniently, the antibodies are conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Multi-color analysis is of interest for the separation of cells based on multiple surface antigens, e.g. RET+, p75+, MASH1+, etc. Fluorochromes which find use in a multi-color analysis include phycobiliproteins, e.g. phycoerythrin and allophycocyanins; fluorescein and Texas red.

In one embodiment of the subject invention the RET antibody is directly or indirectly conjugated to a magnetic reagent, such as a superparamagnetic microparticle (microparticle). Direct conjugation to a magnetic particle is achieved by use of various chemical linking groups, as known in the art. Antibody can be coupled to the microparticles through side chain amino or sufhydryl groups and heterofunctional cross-linking reagents. A large number of heterofunctional compounds are available for linking to entities. A preferred linking group is 3-(2-pyridyldithio) propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, RET antibody is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available.

The antibody is added to a cell sample. The amount of RET antibody necessary to bind a particular cell subset is empirically determined by performing a test separation and analysis. The cells and RET antibody are incubated for a period of time sufficient for complexes to form, usually at least about five minutes, more usually at least about 10 minutes, and usually not more than one hour, more usually not more than about 30 minutes.

The cells may additionally be incubated with antibodies or binding molecules specific for cell surface markers known to be present or absent on neural cells and neural progenitor cells, as outlined herein.

The labeled cells are separated in accordance with the specific antibody preparation. Fluorochrome labeled antibodies are useful for FACS separation, magnetic particles for immunomagnetic selection, particularly high gradient magnetic selection (HGMS), etc. Exemplary magnetic separation devices are described in WO/90/07380, PCT/US96/00953 and EP 438,520, herein incorporated by reference.

The purified cell population may be collected and propagated in any appropriate medium, as is generally described in the Examples.

The subject cell compositions may find use in a variety of ways. By providing for maturation, proliferation and differentiation into one or more selected lineages through specific different growth factors the progenitor cells may be used as a source of committed cells.

The cells may also be used in the identification, isolation and evaluation of factors associated with the differentiation and maturation of neural cells. Thus, the cells may be used in assays to determine the activity of media, such as conditioned media, evaluate fluids for growth factor activity, involvement with dedication of lineages, or the like.

The cells may be used for the treatment of genetic diseases. Genetic diseases associated with neural cells may be treated by genetic modification of autologous or allogeneic stem cells to correct a genetic defect or treat to protect against disease. Examples of PNS disorders in mice include the trembler and shiverer strains. The trembler mutation is thought to involve a defect in the structural gene for myelin basic protein (MBP). This mutation maps to the same region of chromosome 11 as does the MBP gene. This mutation results in the defective myelination of axons in the PNS. An analogous disorder is seen in humans, Charcot-Marie-Tooth syndrome, which results in progressive neuropathic muscular atrophy.

Similarly, the shiverer mutation in mice results in a severe myelin deficiency throughout the CNS and a moderate hypo-myelination in the PNS. Severe shivering episodes are seen 12 days after birth. An analogous disorder is seen in humans, Guillaum-Barre' disease, which is characterized by an acute febrile polyneuritis.

The cells of the invention are introduced into a mammal exhibiting a neurological disorder to examine the therapeutic potential of these cells. These cells are preferably isolated from a mammal having similar MHC genotypes or the host mammal is immunosuppressed using drugs such as cyclosporin A. The cells are injected into an area containing various peripheral nerves known to be effected in a particular mammal or into the spinal cord or brain for mammals which show involvement of the CNS. The cells are injected at a range of concentrations to determine the optimal concentration into the desired site. Alternatively, the cells are introduced in a plasma clot or collagen gel to prevent rapid dispersal of cells from the site of injection. The effect of this treatment on the neurological status of the model animal is noted. Desired therapeutic effects in the above mutant mice include the reduction or cessation of seizures or improved movement of lower motor extremities.

Other diseases may be corrected by introduction of the wild-type gene into the subject cells, either by homologous or random recombination. Alternatively, normal allogeneic progenitor cells may be transplanted. Diseases other than those associated with neural cells may also be treated, where the disease is related to the lack of a particular secreted product such as hormone, enzyme, interferon, factor, or the like.

The cells may be frozen at liquid nitrogen temperatures and stored for long periods of time, being thawed and capable of being reused.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Construction of Lipid-Linked Form of c-RET

Molecular cloning manipulations were performed using standard methods. PI-anchored RET was constructed by methods similar to those used for the expression of a lipid-linked form of the T cell antigen receptor (Devaux, B., Bjorkman, P. J., Stevenson, C., Griof, W., Elliott, J. F., Sagerstrom, C., Clayberger, C., Krensky, A. M. and Davis, M. M., *Eur. J. Immunol.* 21:2111–2119 (1991)). In brief, a DNA segment encoding the murine RET extracellular domain was ligated to a DNA fragment encoding the HPAP-PI anchoring signal (Affimax) and cloned into the expression vector pBJ5 GS. pBJ5 GS contains the glutamine synthetase (GS) gene as a selectable marker and provides a means of gene amplification in the presence of the drug methionine sulfoximine (MSX), a system developed by Celltech, Inc. Amplification in CHO cells was accomplished using 25 uM MSX followed by 100 uM MSX after cloning.

Immunization Procedures and Antibody Screening

Armenian hamsters (Cytogen Research & Development) were immunized with $5\times10^5$ CHO cells per injection and a total of four injections. Three days after the boost, the hamster was sacrificed, and its spleen cells were fused with P3X63Ag8u.1 mouse myeloma cells. Hybridoma supernatants were screened on a subline of murine NIH 3T3 cells stably expressing a high level of the c-RET-PI protein. Positive clones were further tested on transiently transfected 293T cells expressing a cDNA encoding intact RET. Out of five subclones, three clones were able to stain both mouse neuroblastoma Neuro-2a and rat MAH cells (Birren, S. J. and Anderson, D. J., *Neuron* 4:189–201 (1990)).

Isolation and Culture of Primary Rat Enteric Precursor Cells

The fetal gut (including stomach, midgut and hindgut) was dissected from embryonic albino rats (Simonsen Laboratories) at E14.5 and dissociated using 1.5 mg/ml collagenase (Worthington), 1.0 mg/ml elastase (Sigma) and 50 μg/ml DNase I (Sigma). The cells were incubated with a cocktail of three different hamster anti-RET hybridoma supernatants (3A61D7, 3A61C6 and 2C42H1) plus 50 μl/ml DNase I for 30 min at room temperature, followed by a 1:200 dilution of phycoerythrin-conjugated goat anti-mouse IgG (Jackson Immuno Research Laboratories). RET$^+$ cells were isolated on an Epics Elite Fluorescence Activated-Cell Sorter (Coulter) using a multiparametric gate based on fluorescence intensity, size, density and granularity.

The cells were collected into a single round-bottomed well of a 96-well plate. Viable cells were plated at 300 cells per 35 mm dish that had been treated with poly-D-lysine (Biomedical Technologies) and fibronectin (New York Blood Center). Cells were grown in complete NCSC medium containing (among other additives) insulin, epidermal growth factors, basic fibroblast growth factor, NGF and 10% chick embryo extract as described previously (Stemple, D. L. and Anderson, D. J., *Cell* 71:973–985 (1992)). After 15 hr in culture, each individual flat (non-process-bearing) cell was identified by morphology and inscribed with a circle on the bottom of the tissue culture plate. Cells that underwent division during the first 15 hr were rejected from the analysis. Clones were observed and photographed every 24 hr for the first 4 days and scored for the presence of process-bearing neurons. For some experiments, the cultures were carried for 12–14 days, and the medium was further supplemented with rhGGFII (Marchionni et al., *Nature* 362:312–318 (1991) or 10% fetal bovine serum plus 5 μm forskolin (Sigma) to promote Schwann cell differentiation, GGF was added at the time of plating, and fetal bovine serum plus forskolin was added 4 days after plating. Similar results were obtained using either rhGGFII or a partially purified preparation of native bovine GGF from pituitary extracts.

Immunocytochemistry

For internal staining of RET protein, cells were fixed with freshly prepared 4% paraformaldehyde and permeabilized using 0.1% Nonidet P-40. Cells were incubated with anti-RET hybridoma supernatants for 18 hr at 4° C., followed by a 2 hr incubation at room temperature with RG 7/7, a mouse monoclonal anti-rat K chain 1B that is cross-reactive with Syrian and Armenian but not Chinese hamster K chain, followed by a goat anti-mouse tertiary antibody. Staining was visualized using a Vectastain ABC Kit (Vector Labs) with horseradish peroxidase development using diaminobenzidine as substrate. Immunocytochemical staining for MASH1, p75, nestin and neurofilament was carried out as described previously (Stemple, D. L. and Anderson, D. J., *Cell* 71:973–985 (1993); Shah et al., *Cell* 77:349–360 (1994).

RESULTS

RET is Expressed by Neurons but not by NCSCs In Vitro

In situ hybridization experiments have indicated that RET is not expressed by early migrating trunk neural crest cells in vivo but is expressed after these cells have aggregated to form the primordia of autonomic ganglia (Pachnis, V., Mankoo, B. and Costantini, F., *Development* 119, *in press* (1993)). To determine the pattern of RET protein expression by neural crest cells in vitro, primary explants of rat neural crest cells were stained with the monoclonal antibody to RET. No RET staining was detectable in the explants after 24 hr, whereas staining was clearly detectable on some of the neurons that had developed in these cultures after 9 days. These results indicate that in vitro, as in vivo, RET is not expressed by neural crest cells immediately after they emigrate from the neural tube. However, as expected, RET is expressed by at least some of the neurons that derive from the neural crest explants.

Antigenic Phenotype of RET$^+$ Cells Isolated from Fetal Rat Gut

The embryonic day (E) 14.5 fetal gut was chosen as a source of tissue since it is extensively colonized by RET$^+$ neural crest-derived cells (Pachnis et al., *Development* 119, *in press* (1993); Lo et al., *Persp. Dev. Neuro.* 2:191–201 (1994)). This marker represents the earliest detectable cell surface antigen that is expressed by neural crest-derived cells in the gut, but that is not expressed by NCSCs. RET+ cells could be readily separated from unlabeled gut cells by fluorescence-activated cell sorting (FACS), and these constituted about 1% of the population at this stage.

The morphology, antigenic phenotype and functional properties of the RET+ cells isolated from E14.5 gut were characterized. RET+ cells examined 15 hr after plating fell into two morphologically distinct categories; neurons and undifferentiated (flat) cells. Approximately 30% of the cells were neurons, and these cells usually expressed higher levels of RET immunoreactivity than did the flat cells (data not shown). The neuronal subpopulation was not examined further.

To establish their antigenic phenotype, RET+ cells were fixed 15 hr after plating and stained with several antibody markers for neural crest cells and their derivatives; 95% of the flat cells could be relabeled with anti-RET antibody (Table 1) using the immunoperoxidase procedure. The unlabeled cells may represent a minor contaminant, or rather neural crest cells that down-regulated RET expression following their isolation. Almost 100% of the flat cells expressed nestin (Table 1), a neuroepithelial stem cell marker (Lendahl et al, *Cell* 60:585–595 (1990)) also expressed by NCSCs (Stemple, D. L. and Anderson, D. J., *Cell* 71:973–985 (1992)). More than 70% of the cells expressed the low affinity nerve growth factor (NGF) receptor (p 75), a surface marker of NCSCs (Stemple, supra). The majority of the cells were negative for the 160 kDa subunit of neurofilament (Table 1), a neuronal marker, and all of the cells were negative for the glial marker glial fibrillary acidic protein (GFAP; data not shown), as is the case for NCSCs (Stemple, D. L. and Anderson, D. J., *Cell* 71:973–985 (1992)). While the p75+, nestin+, lineage marker (e.g., GFAP, NF160) (lin)– phenotype is characteristic of NCSCs, as discussed above, NCSCs do not express RET. Another difference between NCSCs and RET+ cells was revealed by staining with an antibody to the basic-helix-loop-helix (transcriptional regulator MASH1 (Lo et al, *Genes & Dev.* 5:1524–1537 (1991)). NCSCs do not express this marker; however, 87% of the RET+ cells expressed detectable MASH 1 immunoreactivity (Table 1). Thus, RET+ cells isolated from fetal gut are antigenically distinct from both NCSCs and differentiated neural crest derivatives.

TABLE 1

Antigenic Phenotype of E14.5 Undifferentiated RET+ Enteric Cells

| | Percentage of Nonneuronal Cells Labeled | | | | |
|---|---|---|---|---|---|
| | RET | p75 | Nestin | MASH1 | NF160 |
| + | 58.5% ± 0.5% | 70% ± 1% | 100% | 54.5% ± 5.5% | 16.5% ± 1.5% |
| +/– | 36.5% ± 2.5% | 7.5% ± 7.5% | 0% | 32.5 ± 7.5% | 10% ± 10% |
| + or +/– | 95% | 77.5% | 100% | 87% | 26.5% |

Isolated RET+ cells were plated at clonal density, fixed after 15 hr, and stained for the various antigenic markers indicated. The percentages of strongly labeled (+), weakly labeled (+/–) and unlabeled (–) cells were measured. Approximately 100 cells were scored for each determination. The results represent the mean ± range of two independent experiments. In a separate experiment, the cells were stained for GFAP and no expression was detected.

Functional Properties of Undifferentiated RET+ Cells

To determine the functional properties of the morphologically undifferentiated subset of RET+ cells, individual flat cells were identified and circled 15 hr after plating, after which they were observed every day for the next 3–4 days. In addition, some cultures were allowed to develop for 12 days with or without the addition of 10% fetal bovine serum plus 5 μM forskolin (which have previously been shown to promote the expression of glial differentiation markers in clonal NCSC cultures; Stemple, supra) and were then fixed and stained with neuronal and glial antibody markers. This clonal analysis revealed that the population of undifferentiated RET+ cells contained three functionally distinct subsets. One subset produced clones that consisted of neurons and nonneuronal cells. In some cases, the first 1–3 divisions produced 2–8 flat cells similar to the founder cell, followed by the generation of neurons from some of these cells. In other cases, process-bearing neurons and flat cells were observed within 2 days after plating, suggestive of an initial asymmetric cell division by the founder cell. In all cases, neuronal differentiation was detected morphologically within 3 days. Double labeling of 12 day cultures exposed to serum and forskolin with antibodies to peripherin and GFAP revealed the presence of both neurons and glial cells (as well as other unidentified nonneuronal cells) in these clones. These cells, which we have termed proneuronal progenitors (proNPs), were present at a frequency of 5%–16% of the undifferentiated RET+ cells in two different experiments (Table 2).

TABLE 2

Developmental Potential of RET+ Progenitor Cells in Clonal Culture

| | % NP (n) | % ProNP (n) | % NP or ProNP | % NNP (n) |
|---|---|---|---|---|
| Exp. 1 | 17% (25) | 16% (23) | 33% | 67% (96) |
| Exp. 2 | 35% (78) | 5% (11) | 40% | 60% (135) |
| Mean ± range | 26% ± 9% | 10.5% ± 5.5% | 36.5% ± 3.5% | 63.5% ± 3.5% |

Single RET+ cells were identified 15 hr after plating and observed every 24 hr for the next 4 days. All of the cells initially circled survived this incubation. At the end of this incubation, they were classified as neuronal progenitors (NPs), proneuronal progenitors (proNPs) or nonneuronal progenitors (NNPs), depending upon whether they produced neurons only, neurons plus nonneuronal cells or nonneuronal cells only, respectively. The numbers represent the percentage of each clone type scored, with the raw number of clones of each type given in parentheses. A total of 144 cells were examined in experiment 1 and 224 cells in experiment 2. Note that the variation in the percentage of NP plus proNP cells (±10%) is much smaller than the variation in the percentage of NP or proNP cells individually (±35% and ±52%, respectively).

A second subset of RET+ cells, called nonneuronal progenitors (NNPs), consisted of cells that produced progeny that failed to differentiate into neurons, even when the incubation was extended for nearly 2 weeks (data not shown). To determine whether these nonneuronal cells were glial precursors, we cultured them in 10% fetal bovine serum plus 5 μM forskolin. Under these conditions, some of the cells in the NNP clones expressed GFAP, indicating that these clones contain progenitors of glia and possibly other as yet unidentified nonneuronal cells. In two separate experiments, NNPs constituted 60%–67% of the undifferentiated RET+ cells (Table 2).

A third subset of RET+ cells, termed neuronal progenitors (NPs), consisted of cells that produced 2–8 progeny (1–3 divisions), all of which differentiated to neurons within the first 3–4 days of culture. Moreover, even within relatively large NP clones, neuronal differentiation appeared synchronous. NPs constituted 17%–50% of the undifferentiated cells examined, depending upon the experiment (Table 2; see above). Although the exact frequency of NP and proNP cells varied among experiments, the percentage of NPs was always greater than that of the proNPs (Table 2). We were unable to distinguish between these three different classes of progenitor cells by expression of any of the antigenic markers examined or by their morphology.

To determine the type(s) of neurons produced from NP and proNP cells, some of the cultures were fixed and stained with various antibody markers. Some, but not all, of the neurons were labeled by antibodies to tyrosine hydroxylase and B2 (data not shown), two markers that are transiently expressed by a subset of enteric neuronal progenitors as well as by sympathetic neurons (Carnahan et al., 1991). Unfortunately, there are no markers available that uniquely identify enteric neurons in vitro. All of the neurons that developed expressed higher levels of RET than did their progenitors (data not shown). In vivo, RET is expressed by most or all autonomic neurons and by only a small subset of sensory neurons in the dorsal root ganglia (unpublished data). These data are consistent with the idea that Nps and proNPs generate neurons in one or more autonomic lineages. However, in the absence of appropriate markers, we cannot exclude that these progenitors can give rise to sensory neurons as well.

Anti-RET and Anti-p75 Antibodies Select Different Populations of Enteric Precursors Previously, we used monoclonal antibody 1921 g, directed against the low affinity NGF receptor ($p75^{LNGFR}$), as a surface marker for NCSCs isolated from E10.5 neural tube explants (Stemple and Anderson, 1992). We therefore wished to determine whether this antibody would bind to a similar or different population of neural crest-derived cells in the E14.5 gut than did the anti-RET monoclonal antibody. In parallel assays, approximately 1% of the dissociated E14.5 gut cells were $p75^+$, whereas only 1%–2% of the cells were $RET^+$. When FACS-isolated $p75^+$ cells were plated in clonal culture, identified, and followed every 24 hr, only 6.5%±0.5% of the cells were NPs (mean±range of two independent experiments). By contrast, in parallel cultures seeded with $RET^+$ cells FACS-isolated from the same starting cell suspension, 50%±3% of the cells behaved as NPs. Thus, the $RET^+$ population appeared to be 8- to 9-fold enriched relative to the $p75^+$ population, in NP cells. Consistent with this functional analysis, only 5% of the $p75^+$ cells were $RET^+$ 15 hr after plating, and only 14% were $MASH1^+$. In contrast, 82% of the $RET^+$ cells isolated in parallel were $MASH1^+$ in this experiment. These data support the idea that anti-RET and anti-$p75^{LNGFR}$ antibodies enrich for distinct populations of neural crest-derived cells in the gut. $RET^+$ cells are enriched in both NPs and $MASH1^+$ cells. This correlation supports the idea that many (but not necessarily all) MASH $1^+$ cells are NPs.

NPs Appear Insensitive to GGF and Fibronectin

As described above, some $RET^+$ cells produced only nonneuronal cells or neurons plus nonneuronal cells, whereas others produced only neurons. This apparent heterogeneity could reflect the existence of distinct progenitor cell compartments at different and sequential stages in the lineage segregation process, as suggested for avian neural crest cells in clonal culture (Baroffio et al., 1988; Le Douarin et al., 1991). Alternatively, it may suggest a uniform progenitor population that exhibits clonal variation in developmental fate due to stochastic properties or to subtle variations in the local culture microenvironment. To distinguish between these possibilities, we examined the effect of recombinant human GGFII (rhGGFII; also called neuregulin; Marchionni et al., 1993) on the behavior of these cells. rhGGFII/neuregulin has previously been shown to exert an instructive influence on trunk-derived NCSCs, repressing neuronal differentiation and promoting glial differentiation by most or all of the cells (Shah et al., 1994). If the $RET^+$ enteric progenitor population were developmentally homogeneous but sensitive to local microenvironmental factors, then in the presence of a uniform environmental influence such as GGF, all clones might behave similarly (i.e., neuronal differentiation would be suppressed). On the other hand, if the $RET^+$ population contained some cells committed to a neuronal fate, these cells might be insensitive to the influence of GGF.

Two separate experiments were performed, in which clones derived from morphologically undifferentiated founder cells were followed with (n=97) and without (n=75) GGF. Each clone was examined every day for 3 days to determine whether neurons developed and survived or developed and died. The proportion of NNPs in the cohort of clones examined was virtually identical with or without GGF (62% GGF versus 57% GGF; Table 3), suggesting that GGF was unable to convert proNPs to NNPs by completely inhibiting neuronal differentiation. Similarly, the ratio of NPs to proNPs was comparable in the two experiments (6% versus 9%; Table 3), suggesting that GGF was unable to convert NPs to proNPs by partially inhibiting neuronal differentiation. Positive controls indicated that the preparations of the rhGGFII used in these experiments were active in suppressing neuronal differentiation in both primary neural crest explants and in clonal NCSC cultures (data not shown). The concentrations of rhGGFII used in these experiments were always greater than that required to achieve half-maximal inhibition of neuronal differentiation in clonal cultures of NCSCs (Shah et al., 1994). Together, these data indicate that NPs, proNPs and NNPs maintain their distinct developmental capacities in the presence of rhGGFII, suggesting that they are intrinsically different from one another as well as from neural crest stem cells.

As a further test of the extent of commitment of NPs, we compared their behavior on the standard poly-D-lysine/fibronectin substrate and on a fibronectin substrate. It has previously been demonstrated that neuronal differentiation from NCSCs is strongly inhibited or delayed on a substrate that contains fibronectin but not polylysine (Stemple and Anderson, 1992). In contrast, when $RET^+$ progenitors were plated on fibronectin, a significant number of clones generated neurons after only 48 hr in culture (Table 3, NP clones), indicating that this substrate is unable to inhibit or delay neuronal differentiation of this progenitor cell type. An apparent reduction in the frequency of proNPs and an increase in the frequency of NNPs were observed (Table 3), however, suggesting that neuronal differentiation in multipotent proNP clones might be susceptible to inhibition by fibronectin. On the other hand, these differences could simply reflect differences in the initial attachment of proNPs versus NNPs, rather than a conversion of proNPs to NNPs. The important point, however, is that there were any neurons that differentiated on fibronectin at all; in positive control experiments, neuronal differentiation by NCSCs was completely inhibited by these batches of fibronectin (data not shown). Together, therefore, these data indicate that $RET^+$ NPs differentiate to neurons despite the presence of both soluble factors and extracellular matrix molecules that can inhibit neuronal differentiation by early migrating trunk NCSCs.

Early Migrating Vagal Neural Crest Cells are Sensitive to GGF/Neuregulin

The foregoing data indicated that $RET^+$ postmigratory neural crest cells appear insensitive to GGF/neuregulin, unlike NCSCs (Shah et al., 1994). This difference could be due to temporal or to positional differences between the two populations: $RET^+$ cells from fetal gut not only represent a later stage in development than NCSCs, but in addition derive from the vagal neural crest. By contrast, NCSCs have been previously characterized in cultures from trunk neural crest, which normally does not generate the enteric nervous system in vivo. To distinguish between these two possibilities, we established explants from the vagal neural crest (the region of the first 6–7 somites posterior to the otic placode in E10 rat embryos) and exposed them to GGF. Following 12 days of culture in control medium, the vagal crest explants contained large numbers of neurons expressing peripherin; by contrast, no neurons were observed in explants grown in GGF/neuregulin (data not shown). These data indicate that vagal neural crest cells, like their counterparts in the trunk, are sensitive to the influence of GGF/neuregulin and support the idea that the lack of GGF responsiveness in RET$^+$ postmigratory neural crest cells represents a developmental change rather than a positional difference.

TABLE 3

Effect of GGF and Fibronectin on RET$^+$ Progenitors in Clonal Culture

|  | rhGGFII | | | Control[a] | | |
| --- | --- | --- | --- | --- | --- | --- |
|  | NP | ProNP | NNP | NP | ProNP | NNP |
| Ex. 1/p1 | 9 | 3 | 14 | 9 | 3 | 6 |
| Ex. 1/p2 | 11 | 0 | 12 | 10 | 3 | 12 |
| Ex. 1/p3 | 7 | 3 | 14 | 4 | 1 | 11 |
| Ex. 2/p1 | 12 | 2 | 19 | 5 | 0 | 20 |
| Ex. 2/p2 | 6 | 1 | 22 | 6 | 3 | 12 |
| Ex. 2/p3 | 4 | 1 | 16 | 11 | 2 | 12 |
| Total | 49 | 10 | 97 | 45 | 12 | 75 |
| Percentages of all clones | 31% | 6% | 62% | 31% | 9% | 57 |

RET$^+$ enteric cells were plated at clonal density and then cultured for 12 days in the presence or absence of rhGGFII (lot #92893) at a concentration of 89 ng/ml (~1.5 nM). This dose is 5 times that required to achieve half-maximal inhibition of neuronal differentiation in NCSC clonal cultures (Shah et al., 1994); similar results were obtained in other experiments (data not shown) using twice this concentration.
At the end of the incubation, the proportions of NP, proNP and NNP clones were determined retrospectively as in Table 2. The results are derived from two independent experiments in which cultures were analyzed in triplicate (e.g., "Ex. 1/p1" indicates experiment 1, plate 1, etc.). Note that the average percentage of each progenitor cell type is virtually identical with or without rhGGFII.
Similar results were obtained with a second independent lot of rhGGFII (data not shown.) Note that the results with fibernectin derive from two independent experiments (Ex. 1 and Ex. 2). Positive control experiments indicated that those batches of fibronectin produced effective inhibition of neuronal differentiation in clonal cultures of NCSCs.
[a]Cultures were grown on a standard fibronectin/poly-D-lysine substrate in the absence of rhGGFII.
[b]Plates were coated with fibronectin only, rather than with fibronectin plus poly-D-lysine.

In conclusion, the RET$^+$ neural crest cells isolated from E14.5 gut contained four distinct but apparently related cell types: postmitotic, process-bearing neurons; multipotent progenitors or neurons and nonneuronal (glial) cells (proNPs); nonneuronal progenitor cells (NNPs); and committed neuronal progenitors (NPs). The simplest interpretation of these data is that the four cell types represent distinct stages in a common lineage that are present contemporaneously in the developing gut. Although this is not formally proven, it is well established that the differentiation of the enteric nervous system is asynchronous (Pham, T. D., Gershon, M. D. and Rothman, T. P., J. Comp. Neurol. 314:789–798 (1991)), so that at E14.5 both differentiated neurons and undifferentiated progenitors should coexist in the gut.

The identification of proNPs in the E14.5 gut provides direct evidence that multipotent progenitors of neurons and glia persist in the mammalian gut long after neural crest migration has ended, consistent with recent results in the avlan system (Deville et al. Dev. Biol. 163:141–151 (1994)). Previous studies have reported the development of neurons and glia from populations of crest-derived cells immunoselected from fetal rat gut using other antibody markers, but no clonal analysis was performed to determine whether neurons and glia arose from separate or common progenitors (Pomeranz et al., Dev. Biol. 156:341–361 (1993); Chalazonitis et al., J. Neurosci. 14:6571–6584 (1994)). It will be interesting to determine whether multipotent neural progenitors in the gut persist into adulthood, as has been demonstrated for their counterparts in the CNS (Reynolds et al., Science 255:1707–1710 (1992); Lois, C. and Alvarez-Buylla, A., Proc. Natl. Acad. Sci. USA 90:2074–2077 (1993)).

While the developmental potential of proNPs from E14.5 gut is similar to that of NCSCs isolated from E10.5 neural tube explants, several lines of evidence suggest that these two multipotent progenitor cell types are functionally and antigenically distinct. First, proNPs were isolated on the basis of RET expression, and NCSCs do not express RET immunoreactivity. Second, at least some proNPs may express MASH1 (see below). NCSCs, by contrast, are MASH1$^-$ (Shah et al., Cell 77:349–360 (1994)). Third, neuronal differentiation in NCSC clones is repressed by GGF and fibronectin, whereas in proNPs it is apparently insensitive to these environmental influences. Finally, NCSCs appear to undergo at least 6–10 rounds of symmetric, self-renewing division before the emergence of distinct neuronal and glial lineages (Stemple, D. L. and Anderson, D. J., Cell 71:973–985 (1992)). By contrast, proNPs generate progeny that differentiate to neurons after only a few divisions. Together, these data suggest that the properties of proNPs are distinct from those of NCSCs. The fact that vagal neural crest cells respond to GGF/neuregulin as do their trunk counterparts, moreover, argues that these distinct properties reflect differences in developmental stage rather than in position of origin along the neuraxis.

The use of anti-RET antibodies allowed enrichment for and identification of an apparently committed neuronal progenitor cell (called NP) in the enteric precursor population. For comparison, such NPs were 8–9 times more enriched in the RET$^+$ population than in a population isolated using another surface marker of neural crest cells, p75$^{LNGFR}$. The fact that NPs can be recovered at all using anti-p75 antibodies makes it highly unlikely that the anti-RET antibodies induced neuronal commitment, e.g., by mimicking ligand activation of the receptor. Furthermore, if this were the case, one might have expected 100% of the RET$^+$ cells to behave as NPs; in fact, many (50%–60%) did not.

The existence of committed neuronal progenitors in the CNS has been suggested previously, based on studies of cortical (Davis, A. and Temple, S., Nature 372: 263–266 (1994)) or striatal (Vescovi et al., Neuron. 11:951–966 (1993)) neuroepithelial cells grown in clonal cultures. However, in those cases the cells were not "challenged" by exposure to environmental factors know to suppress neuronal differentiation by multipotent stem cells. Here we have shown that NPs appear insensitive to GGF and fibronectin, environmental factors that suppress neuronal and promote glial differentiation by trunk NCSCs (Stemple, D. L. and Anderson, D. J., Cell 71:973–985 (1992); Shah et al.,(1994)). This strongly suggests that NPs are committed to a neuronal fate, although whether these neurons are committed to an enteric or autonomic lineage is presently unclear.

A number of earlier studies have been interpreted to suggest that neural crest cells undergo progressive restriction in their developmental capacities (reviewed in Anderson, D. J., Curr. Opin. Neurobiology 3:8–13 (1993)). However, in cases where neural crest cell populations were challenged by exposure to a different environment (e.g., by in vivo transplantation [Le Lievre, C. S., Schweizer, G. G., Ziller, C. M. and Le Douarin, N. M., Developmental Biology. 77:362–378 (1980)] or explantation in vitro [Artinger, K. B. and Bronner-Fraser, M., Dev. Biol. 149:149–157 (1992)], analysis was not performed at the single-cell level. Conversely, in cases where postmigratory neural crest cells were analyzed in clonal cultures (Duff, et al., Dev. Biol. 147:451–459 (1991); Deville, et al., Dev. Brain Res. 66:1–10 (1992); Deville et al., Dev. Biol. 163:141–151 (1994) or by retroviral marking (Hall, A. K. and Landis, S. C., Neuron 6:741–752 (1991)), the cells were not challenged by exposure to different environmental signals. In the present study, we have challenged postmigratory neural crest cells in clonal cultures with environmental signals previously shown to control the fate of multipotent cells. The identification of committed neuron progenitors using RET as a marker now opens the way to reconstituting the commitment process in vitro, beginning with committed NCSCs.

Like NCSCs, proNPs are multipotent; unlike NCSCs, however, their progeny rapidly segregate into neurogenic and nonneurogenic lineages. This implies that either division or differentiation of these cells must be asymmetric. Such asymmetry may not be intrinsic to the cell division itself, but rather may be conferred by differences in the local microenvironment encountered by two otherwise equivalent daughter cells. Alternatively, the division could be intrinsically asymmetric and generate two nonequivalent daughter cells, such as has been demonstrated for the first division of the sensory mother cell in the Drosophila PNS (Posakony, J. W., Cell 76:415–418 (1994)). It will be interesting to see whether proNPs express vertebrate homologs of numb (W. M. Zhong and Y. N. Jan, personal communication), a Drosophila gene required for the asymmetric division of the sensory mother cell (Uemura, et al., Cell 58:349–360 (1989)) whose protein product is asymmetrically distributed prior to cytokinesis (Rhyu et al., Cell 76:477–492 (1994)).

NP clones contain only neurons. In principle, such clones could be produced either by asymmetric divisions of a stem cell that generated a postmitotic neuroblast and another stem cell at each division until the stem cell was consumed or died, or rather by symmetric divisions of a committed neuroblast. A log plot of NP clone size as a function of time yields a straight line with a slope of 2 (data not shown). This indicates that NP clones expand by symmetric rather than asymmetric (stem cell-like) divisions, analogous to erythroblasts (for example) in the hematopoietic lineage (Briegel, et al., Genes Dev. 7:1097–1109 (1993)). Symmetrically dividing progenitors have also been identified in the CNS oligodendrocyte lineage (Temple, S. and Raff, M. C., Cell 44:773–779 (1986)). Whether here, as in that system, an intrinsic limitation on the number of cell divisions represents a mechanism for controlling the timing of differentiation remains to be determined.

Both Ret and Mash1 are regulatory genes essential for the development of subsets of autonomic neurons, as shown by targeted gene disruption experiments in mice (Guillemot, F. and Joyner, A. L. (1993), Mech. Devel. 42:171–185 (1993); Schuchardt, et al., Nature 367:380:383 (1994)). In addition, both genes are initially expressed in otherwise morphologically and antigenically undifferentiated neural crest cells (Lo et al., Genes & Dev. 5:1524–1537 (1991); Guillemot, F. and Joyner, A. L., Mech. Devel. 42:171–185 (1993); Pachnis et al., Development 119, in press (1993). While Ret is genetically essential for the development of all enteric neurons, the precise developmental operation it controls is not yet established. Our data indicate that some $RET^+$ cells (proNPs and NNPs) are not yet committed to a neuronal fate. This leaves open the possibility that RET signaling could trigger the commitment of multipotent neural crest cells to a neuronal fate, analogous to the role of the sevenless protein in Drosophila photoreceptor cell fate determination (for review, see Rubin, G. M., Trends Genet. 7:372–377 (1991)). By contrast, if RET were expressed only by neurons or by NPs, a function in neuronal lineage commitment could be excluded.

Similarly, the fact that the majority of $RET^+$ cells express MASH1 suggests that at least some of these $MASH1^+$ cells are multipotent as well. In this case, however, the argument is indirect (statistical) because MASH1 is a nuclear protein and its expression cannot be assessed without fixing and killing the cells. Nevertheless, since almost 90% of $RET^+$ cells are $MASH1^+$, and since close to 70% of $RET^+$ cells are either NNPs or proNPs (Table 2), it is apparent that MASH1 is expressed by some cells that are not yet committed to a neuronal fate. As in the case of RET, this would allow a potential function for MASH1 in the commitment of cells to a neurogenic lineage. However, recent data using cell lines derived from Mash1 mutant mice suggest that MASH1 function is required only after cells are committed to a neuronal fate (L. Sommer, N. Shah, M. Raeo and D. J. A., unpublished data), although the present data suggest that the protein is expressed before such commitment occurs.

The fact that Ret and Mash1 are expressed sequentially (Guillemot, F. and Joyner, A. L., Mech. Devel. 42:171–185 (1993); Lo, L., Guillemot, F., Joyner, A. L. and Anderson, D. J., Persp. Dev. Neuro. 2:191–201 (1994)) in the same cells and that both are required for the differentiation of at least a subpopulation of peripheral autonomic neurons raises the possibility that there is an interaction between these two genes. For example, signaling through RET could lead to the expression of MASH 1; conversely, MASH1 could be required for the maintenance or up-regulation of RET expression. However, though Ret is required for the differentiation of all enteric neurons (Schuchardt, A., D'Agati, V., Larsson-Blomberg, L., Costantini, F. and Pachnis, V., Nature 367:380–383 (1994)), it is not essential for the initial differentiation of sympathetic neurons (V. Pachnis, personal communication). Conversely, Mash1 is required for sympathetic neuron differentiation (Guillemot, F. and Joyner, A. L., Mech. Devel. 42:171–185 (1993)) but not for the differentiation of some enteric neurons. These data suggest that Mash1 expression does not require Ret function in sympathetic neurons, and that Ret function does not require Mash1 expression in late-generated enteric neurons. Nevertheless, recent evidence indicates that early-generated enteric neurons, including the serotonergic subset, require Mash1 function (Blaugrund et al., submitted) as well as Ret function (Schuchardt, A., D'Agati, V., Larsson-Blomberg, L., Costantini, F. and Pachnis, V., Nature 367:380:383 (1994)). This leaves open the possibility that there is a genetic interaction between Ret and Mash1 within this enteric sublineage. The ability to isolate $RET^+$ neural crest cells from embryos of various genotypes should permit a more detailed analysis of the functions and interactions of Ret, Mash1 and other regulatory genes involved in neural crest development, as well as of the mechanistic basis of developmental restriction within this population.

We claim:

1. A method for the enrichment of neural progenitor cells comprising RET protein, said method comprising:
   a) combining a mixed population of cells comprising neural-crest derived cells comprising neural progenitor cells with an antibody that specifically binds to at least part of an extracellular sequence of said RET protein; and
   b) selecting for RET positive cells which include multipotent cells that are insensitive to neuregulin, whereby the mixed population of cells is enriched for neural progenitor cells.

2. The method according to claim 1 wherein said antibody is selected from the group of consisting of polyclonal antibody, monoclonal antibody fragments, and single chain antibody.

3. The method according to claim 2, wherein said antibody is fluorochrome conjugated.

4. A method according to claim 3, wherein said selecting with said flurochrome conjugated antibody is by flow cytometry.

5. A method for the enrichment of neural progenitor cells, said method comprising:
   a) combining a mixed population of cells comprising neural-crest derived cells comprising neural progenitor cells comprising RET protein with an antibody that specifically binds to at least part of an extracellular sequence of said RET protein; and
   b) selecting for RET positive cells which include multipotent cells that are insensitive to neuregulin, whereby the mixed population of cells is enriched for neural progenitor cells.

6. A substantially pure population of neural crest derived neural progenitor cells comprising RET protein prepared using the method of claim 5, where said cells are proneuronal progenitor (proNP) cells, neuronal progenitor (NP) cells and/or nonneuronal progenitor (NNP) cells, and where said cells include multipotent cells that are insensitive to neuregulin.

7. The population according to claim 6 wherein said neural progenitor cells are bound to an antibody that specifically binds to RET antigen.

8. The population according to claim 7 or 6 wherein said antibody is selected from the group consisting of polyclonal antibody, monoclonal antibody, antibody fragments, and single chain antibody.

9. The population according to claim 8 wherein said antibody is a monoclonal antibody.

* * * * *